United States Patent
Cantrell, Jr. et al.

(10) Patent No.: US 10,493,062 B2
(45) Date of Patent: Dec. 3, 2019

(54) SYNTHESIS OF CYCLOCREATINE AND ANALOGS THEREOF

(71) Applicant: Lumos Pharma, Inc., Austin, TX (US)

(72) Inventors: William R. Cantrell, Jr., San Anotnio, TX (US); William E. Bauta, San Anotnio, TX (US)

(73) Assignee: Lumos Pharma, Inc., Austin, TX (US)

( * ) Notice: Subject to any disclaimer, the term of this patent is extended or adjusted under 35 U.S.C. 154(b) by 0 days.

(21) Appl. No.: 15/506,014

(22) PCT Filed: Sep. 1, 2015

(86) PCT No.: PCT/US2015/047880
§ 371 (c)(1),
(2) Date: Feb. 23, 2017

(87) PCT Pub. No.: WO2016/036699
PCT Pub. Date: Mar. 10, 2016

(65) Prior Publication Data
US 2017/0273950 A1    Sep. 28, 2017

Related U.S. Application Data

(60) Provisional application No. 62/045,177, filed on Sep. 3, 2014.

(51) Int. Cl.
| | |
|---|---|
| C07D 233/46 | (2006.01) |
| A61K 31/4168 | (2006.01) |
| A61K 31/675 | (2006.01) |
| C01C 3/16 | (2006.01) |

(52) U.S. Cl.
CPC ........ *A61K 31/4168* (2013.01); *A61K 31/675* (2013.01); *C07D 233/46* (2013.01); *C01C 3/16* (2013.01)

(58) Field of Classification Search
CPC .................................................. C07D 233/46
See application file for complete search history.

(56) References Cited

U.S. PATENT DOCUMENTS

| | | |
|---|---|---|
| 5,321,030 A | 6/1994 | Kaddurah-Daouk et al. |
| 2008/0242639 A1 | 10/2008 | Ahmed et al. |
| 2010/0303840 A1 | 12/2010 | Kaddurah-Daouk et al. |

FOREIGN PATENT DOCUMENTS

| | | |
|---|---|---|
| CN | 103923014 A | 7/2014 |
| WO | 9312781 A2 | 9/1993 |

OTHER PUBLICATIONS

No new references.*
The International Search Report and Written Opinion, dated Dec. 4, 2015, in the corresponding PCT Appl. No. PCT/US2015/047880.
The extended European search report, dated Jan. 3, 2018, in the corresponding European Appl. No. 15837263.1.
Smejkal et al., "Transition-State Stabilization by a Secondary Substrate-Ligand Interaction: A New Design Principle for Highly Efficient Transition-Metal Catalysis," Chemistry—A European Journal, vol. 16, 2010, pp. 2470-2478.
The English translation of the Chinese Office Action, dated Feb. 3, 2019, in the related Chinese Appl. No. 201580047429.9.
Smejkal et al. "Transition-state stabilization by a secondary substrate-ligand interaction: a new design principle for highly efficient transition-metal catalysis," Chemistry. Feb. 22, 2010;16(8):2470-8. (Abstract).
The U.S. Office Action, dated Jan. 10, 2019, in the related U.S. Appl. No. 16/107,103.

* cited by examiner

*Primary Examiner* — Shawquia Jackson

(57) ABSTRACT

Provided herein is a process for the preparation of a compound of formula (I) or a pharmaceutically acceptable salt thereof, using cynamide in the reaction.

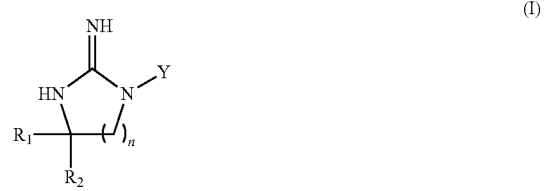

(I)

7 Claims, No Drawings

SYNTHESIS OF CYCLOCREATINE AND ANALOGS THEREOF

CROSS-REFERENCE TO RELATED APPLICATIONS

This application is a National Stage Application of PCT/US2015/047880 filed Sep. 1, 2015, which claims priority from U.S. Provisional Patent Application No. 62/045,177, filed on Sep. 3, 2014. The priority of both said PCT and U.S. Provisional Patent Application are claimed. Each of prior mentioned applications is hereby incorporated by reference herein in its entirety.

FIELD OF THE INVENTION

The invention relates to a chemical process for the preparation of cyclocreatine and related cyclic creatine analogs with application in the treatment of creatine transporter deficiency.

All documents cited or relied upon below are expressly incorporated herein by reference.

BACKGROUND OF THE INVENTION

Cyclocreatine ((2-iminoimidazolidin-1-yl)acetic acid) is used in the treatment of creatine transporter defect. In this genetic disease, a mutation affects the creatine transporter thereby preventing creatine from crossing the blood-brain barrier (BBB), leading to a deficiency of this important amino acid in the brain. Creatine is a polar small molecule and requires active transport to cross the BBB. By contrast, cyclocreatine is more lipophilic owing to its two additional methylene groups and is able to cross the BBB by passive diffusion, thereby functioning as a creatine surrogate.

The synthesis of cyclocreatine was first reported in Rowley, G. L.; Greenleaf, A. L.; Kenyon, G. L. *J. Am. Chem. Soc.* 1971, 93, 5542-5551. The synthesis and characterization of cyclocreatine salts with pharmaceutically acceptable acids was later described in WO 2006/073923. The Rowley synthesis of cyclocreatine starts from the sodium salt of N-carboxymethyl-1,2-diaminoethane. This intermediate is maintained in solution and reacted with a methanolic solution of cyanogen bromide to afford the crude product, which is isolated by filtration from the reaction mixture. Final recrystallization is performed from water to afford the purified product.

The Rowley synthesis, however, is limited by poor overall yield. Further, the use of cyanogen bromide, a highly toxic and reactive compound, requires significant engineering controls for use on scale. More specifically, cyanogen bromide is a low-melting solid with a significant vapor pressure (mp=50-53° C., bp=61-62° C.) and is toxic by inhalation, dermal exposure, and oral ingestion. Indeed, plasma levels of 2.5 µg/mL cause convulsions and death in mice.

A need exists in the art, therefore, for a new synthesis of cyclocreatine and analogs thereof that is less toxic and provides for products in greater yield and at a lower commercial cost.

SUMMARY OF THE INVENTION

The present invention is directed to a process for the preparation of a compound of formula (I):

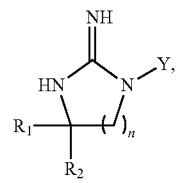

(I)

or a pharmaceutically acceptable salt thereof, comprising the step of reacting a compound of formula (II):

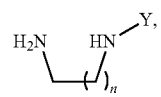

(II)

with a compound of formula (III):

$$H_2N-\equiv N \qquad (III),$$

wherein:
Y is $CH_2CO_2H$, $CH_2CONR_1R_2$ or $CH_2CO_2R_1$;
$R_1$, $R_2$, independently of each other, is hydrogen, lower alkyl, $C_7$-$C_{12}$ alkyl or lower cycloalkyl; and
n is 1, 2, 3, 4 or 5.

DETAILED DESCRIPTION

The present invention is directed at an improved synthetic method for making cyclocreatine and other cyclic creatine analogs in greater overall yield and with improved safety. Cyanamide is a readily available commodity chemical and is significantly less toxic than cyanogen bromide.

The details of the invention are set forth in the accompanying description below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

The following definitions are used in connection with the invention:

The articles "a" and "an" are used in this disclosure to refer to one or more than one (i.e., to at least one) of the grammatical object of the article. By way of example, "an element" means one element or more than one element.

The term "and/or" is used in this disclosure to mean either "and" or "or" unless indicated otherwise.

"Lower alkyl" or "$C_1$-$C_6$ alkyl" refers to a straight or branched chain saturated hydrocarbon containing 1-6 carbon atoms. Examples of a lower alkyl group include, but are not limited to, methyl, ethyl, propyl, butyl, pentyl, hexyl, isopropyl, isobutyl, sec-butyl, tert-butyl, isopentyl, and neopentyl.

"$C_7$-$C_{12}$ alkyl" refers to a straight or branched chain saturated hydrocarbon containing 7-12 carbon atoms.

The term "cycloalkyl" refers to a cyclic hydrocarbon containing 3-6 carbon atoms. Examples of a cycloalkyl group include, but are not limited to, cyclopropyl, cyclobutyl, cyclopentyl and cyclohexyl.

It is understood that any of the substitutable hydrogens on a lower alkyl, $C_7$-$C_{12}$ alkyl or cycloalkyl can be substituted independently with one or more substituents, for example 1, 2 or 3 substituents. Examples of substituents include, but are not limited to, halogen, $C_1$-$C_3$ alkyl, hydroxyl, alkoxy, oxo and cyano groups.

A "patient" is a mammal, e.g., a human, mouse, rat, guinea pig, dog, cat, horse, cow, pig, or non-human primate, such as a monkey, chimpanzee, baboon or rhesus monkey, and the terms "patient" and "subject" are used interchangeably herein.

Representative "pharmaceutically acceptable salts" include, e.g., water-soluble and water-insoluble salts, such as the acetate, amsonate (4,4-diaminostilbene-2, 2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fumarate, gluceptate, gluconate, glutamate, glycollylarsanilate, hexafluorophosphate, hexylresorcinate, hydrabamine, hydrobromide, hydrochloride, hydroxynaphthoate, iodide, isothionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate (1,1-methene-bis-2-hydroxy-3-naphthoate, einbonate), pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts. Additional pharmaceutically acceptable salt forms at the carboxylate function would include lithium, sodium, and potassium.

A "therapeutically effective amount" when used in connection with cyclocreatine is an amount effective for treating or preventing a cyclocreatine-regulated disease or disorder.

It will be understood by those skilled in the art, with respect to any group containing one or more substituents, that such groups are not intended to introduce any substitution or substitution patterns that are sterically impractical, synthetically non-feasible and/or inherently unstable. Furthermore, combinations of substituents and/or variables within any of the Formulae represented herein are permissible only if such combinations result in stable compounds or useful synthetic intermediates wherein stable implies a reasonable pharmologically relevant half-life at physiological conditions.

Scheme 1

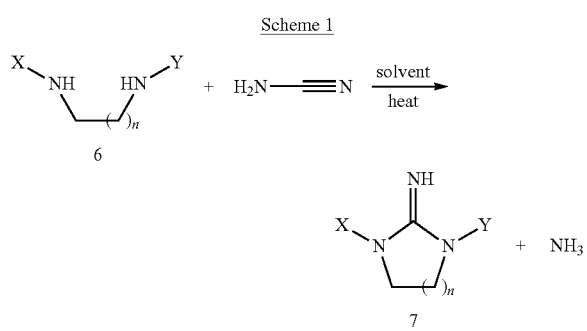

As seen in Scheme I above, the present invention describes a method for the preparation of various cyclic analogs of creatine (7) by the condensation of diamines or their salts (6) with cyanamide in a suitable solvent to afford 7 and ammonia or a salt thereof. In one embodiment of the invention, 6 (X=H, Y=$CH_2CO_2H$, n=1) is reacted with cyanamide in ethanol at 25-100° C. to afford 7 (X=H, Y=$CH_2CO_2H$, n=1). The diamine 6 may be a purified substance or a mixture containing approximately 20-95% 6. The product 7 may, in some embodiments, be further purified by crystallization from water or another suitable solvent to afford 7 in ≥97% chemical purity. Alternate embodiments of 7 can include compounds of formula:

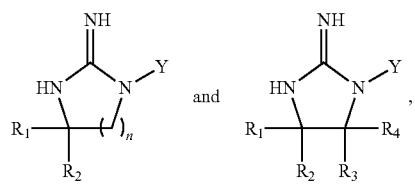

wherein R1, R2, R3, R4, independently of each other, can be hydrogen, lower alkyl or cycloalkyl, or a pharmaceutically acceptable salt thereof.

Thus, in one embodiment, provided is a process for the preparation of a compound of formula (I):

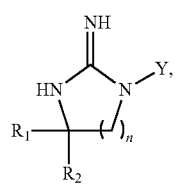

(I)

or a pharmaceutically acceptable salt thereof, comprising the step of reacting a compound of formula (II):

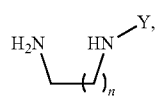

(II)

with a compound of formula (III):

$H_2N$—≡N    (III), wherein:
Y is $CH_2CO_2H$, $CH_2CONR_1R_2$ or $CH_2CO_2R_1$;
$R_1$, $R_2$, independently of each other, is hydrogen, lower alkyl, $C_7$-$C_{12}$ alkyl or lower cycloalkyl; and
n is 1, 2, 3, 4 or 5.

In another embodiment of the present invention, provided is a process for the preparation of a compound of formula (I), wherein a carbon within the parentheses in the compound of formula (I) is optionally substituted with $R_3$ and $R_4$, each of which independently of each other is hydrogen, lower alkyl or cycloalkyl.

In another embodiment of the present invention, provided is a process for the preparation of a compound of formula (I), wherein n is 1.

In another embodiment of the present invention, provided is a process for the preparation of a compound of formula (I), wherein the compound of formula (I) is cyclocreatine or a pharmaceutically acceptable salt thereof.

In another embodiment of the present invention, provided is a process for the preparation of a compound of formula (I), wherein said compound is a compound of formula (Ia):

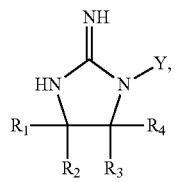

wherein:
Y is $CH_2CO_2H$, $CH_2CONR_1R_2$ or $CH_2CO_2R_1$;
$R_1$, $R_2$, $R_3$, $R_4$, independently of each other, is hydrogen, lower alkyl, $C_7$-$C_{12}$ alkyl or cycloalkyl, or a pharmaceutically acceptable salt thereof.

In another embodiment of the present invention, provided is a process for the preparation of a compound of formula (I), further comprising a precursor step of reacting ethylenediamine with chloroacetic acid to produce said compound of formula (II).

In another embodiment of the present invention, provided is a process for the preparation of a compound of formula (I), wherein the concentration of cyanamide is 1-20 molar equivalents relative to a molar charge of chloroacetic acid.

EXAMPLES

The disclosure is further illustrated by the following examples, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Example 1

Preparation of Intermediate 3 in MTBE

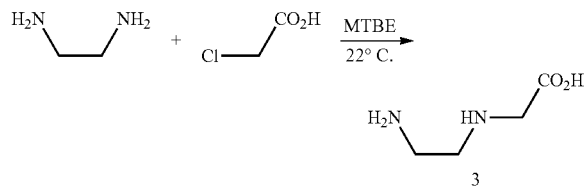

A 500 mL flask was charged with ethylenediamine (62.03 g, 1032 mmol). A solution of chloroacetic acid (6.502 g, 68.80 mmol) in tert-butyl methyl ether (MTBE, 30 mL) was added with magnetic stirring at 22° C. over 0.5 h. The internal temperature had risen to 41° C. during the addition. After stirring an additional 40 min, toluene (100 mL) was added and the mixture concentrated by rotary evaporation; this procedure was done twice more and the resultant residue further dried under high vacuum to afford 16.4 g crude product. The product composition, as evaluated by HPLC/MS was 3 (37.3%), and the corresponding diacid (62.7%).

Example 2

Preparation of Intermediate 3 in Toluene

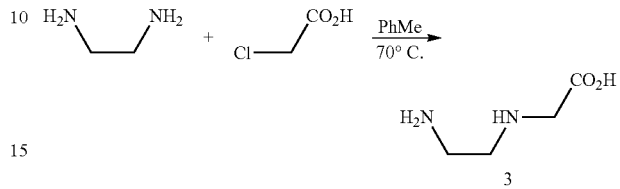

A 40 mL vial with a stopper and magnetic stir bar was charged with ethylenediamine (9.2 g, 153.7 mmol). A syringe pump was charged with a solution of chloroacetic acid (0.968 g, 10.24 mmol) in PhMe (total volume 9.5 mL). The syringe pump was set to deliver at a rate of 19.0 mL/h. The vial containing the ethylenediamine was heated in an aluminum heating block to 70° C. and the addition initiated at this time. After the addition was complete (~30 min), the vial was removed from the heating block and cooled to room temperature. The supernatant layer of liquid was removed by pipette and the remainder evaporated under high vacuum. HPLC/MS analysis of the residue revealed 92.8% monoacid 3 and 7.2% diacid.

Example 3

Preparation of Cyclocreatine From 3 and Cyanamide

A portion of the crude batch of 3 described in Example 1 (5.32 g) was charged to a 100 mL round bottom flask with a stir bar as a solution in $H_2O$ (7.6 mL). Solid cyanamide (1.447 g, 34.41 mmol) was charged as a solid and the flask fitted with a reflux condenser and placed in a 70° C. oil bath. After stirring 20 h, the mixture was cooled to room temperature and the solid filtered, washed with $H_2O$ (2 mL) and dried under high vacuum to afford crude cyclocreatine (1.161 g, ~23.5% yield). HPLC/MS analysis of this solid revealed 99.3% of cyclocreatine, 0.7% of monoacid 3, and none of the diacid. The crude product (1.009 g) was charged to a vial and $H_2O$ (4.147 g) added. The mixture was heated to boiling but this did not result in complete dissolution of the solid. An additional charge of $H_2O$ (3.643 g) with continued heating led to complete dissolution (7.1 mL/g water added for dissolution). The mixture was cooled after 3 h heating and the resultant solid filtered and washed with $H_2O$ (2 mL). Drying under vacuum afforded pure cyclocreatine (0.498 g, 10.1% yield).

Example 4

Preparation of Cyclocreatine Via Reaction with Cyanamide

A 250 mL flask, equipped with mechanical stirrer, was charged with ethylenediamine (28.08 g, 467.3 mmol) and the flask was heated to 70° C. A solution of chloroacetic acid (2.944 g, 31.15 mmol) in toluene (28 mL) was added to the reaction over 30 minutes. The mixture was cooled to ambient temperature and stirring was stopped. The top layer containing toluene and ethylenediamine was removed. Toluene (15 mL) was added to the reaction and the mixture was stirred. Stirring was stopped and the top layer was removed. Toluene (15 mL) was added and the reaction mixture was concentrated. Isopropanol (30 mL) was added and the mixture was cooled to <0° C. and held for 3 days. The reaction mixture was concentrated and ethanol (20 mL) was added. The resulting slurry was filtered and the flask and solids were washed with ethanol. The solids were dried by high vacuum to give 3 (1.286 g, 27%) $^1$H NMR (400 MHz, $D_2O$) δ 3.32 (s, 2H), 3.07 (t, 2H, J=6 Hz), 2.95 (t, 2H, J=6 Hz). None of the di-acid isomers were detected by NMR. A 40 mL vial with magnetic stirbar was charged with compound 3 (1.224 g, 7.918 mmol) and water (8.7 mL). Cyanamide (0.333 g, 7.918 mmol) was added as a solid. The mixture was heated to 70° C. and stirred for 3.5 hours. Analysis by LCMS showed 57% conversion. More cyanamide (0.266 g, 6.327 mrnol) was added and the mixture was stirred at 70° C. for 24 hours. The reaction mixture was cooled to 0° C. and filtered. The vial and solids were washed with water (1 mL). The solids were dried to give cyclocreatine 2 (0.655 g, 58% yield).

Example 5

Preparation and Isolation of [(2-Aminoethyl)Amino]Acetic Acid (3)

A 250 mL, 3 neck flask, equipped with a mechanical stirrer, stopper, and septum, was charged with ethylenediamine (EDA, 67 mL, 1003 mmol). A 30 mL syringe was charged with a solution of chloroacetic acid (CSA, 9.48 g, 100.3 mmol) in DMSO (total volume was 26 mL). The syringe was placed onto a syringe pump set to deliver 3.3 mL/h (total addition time was 8 h). The syringe needle was inserted into the flask via the septum and placed below the level of EDA. Addition occurred at ambient temperature. After addition was complete the reaction mixture was stirred for 10 h at ambient temperature. The reaction mixture was concentrated (60° C., ~10 mbar) to 47 g. Toluene (50 mL) was added and the mixture was concentrated in order to azeotrope EDA. More toluene (50 mL) was added and the mixture was concentrated to 41 g. DMSO (30 mL) was added and the mixture was cooled in an ice/water bath for 30 min. The cooling bath was removed and the mixture was stirred at ambient temperature for 30 min. The mixture was filtered. The flask and solids were washed sequentially with DMSO (50 mL), isopropanol (50 mL), and t-butylmethyl ether (50 mL). The solids were dried under vacuum to give 3 as a white powder (8.74 g, 62%). $^1$H NMR (400 MHz, $D_2O$) δ 3.11 (s, 2H), 2.90-2.70 (m, 4H). MS [M+H]$^+$ m/z 119.1.

Example 6

Preparation of Cyclocreatine 2 From Isolated 3

A 250 mL, 3 neck flask, equipped with a mechanical stirrer, reflux condenser and stopper, was charged with 3 (8.74 g, 74 mmol) and water (10 mL). A solution of cyanamide (4.4 mL, 50 wt % in water) was added and the mixture was heated to 70° C. in an oil bath for 4 h. Heating was discontinued and the mixture was stirred at ambient temperature for 19 h. The mixture was cooled in an ice/water bath and stirred for 2 h. The mixture was filtered and the flask and solids were washed with cold water (5 mL). The solids were dried under high vacuum to give 2 as a white powder (2.88 g, 36%). $^1$H NMR (400 MHz, $D_2O$) δ 3.78 (s, 2H), 3.66-3.60 (m, 2H), 3.57-3.51 (m, 2H). MS [M+H]$^+$ m/z 144.1.

Example 7

Preparation of Cyclic Creatine analog ((2-iminotetrahydro-pyrimidin-1(2H)-yl)acetic Acid

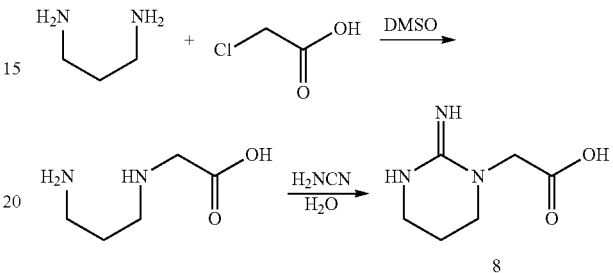

A solution of chloroacetic acid (1 equivalent) in DMSO is added to propane-1,3-diamine (10 equivalents) over a period of 8 hours. The reaction mixture is concentrated by vacuum distillation and DMSO is added. The mixture is cooled to 0° C., and then warmed back up to ambient temperature. The resulting slurry is filtered, and the flask and solids are washed sequentially with DMSO, isopropanol, and t-butylmethyl ether. The solids are dried and dissolved into water. Cyanamide (50 wt % solution in water, 1 equivalent) is added and the mixture is heated to 70° C. for 2 h. The reaction is cooled to 0° C. and the resulting slurry is filtered. The flask and solids are washed with water and dried to give 8.

Example 8

Alternative Embodiment

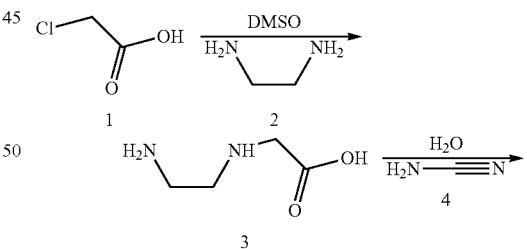

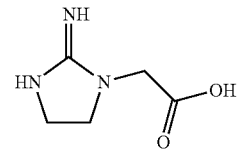

This synthesis is similar to the manufacturing process with the exception of the final purification, where two additional purification operations were conducted: an additional aqueous slurry and a recrystallization from water. In the first step, chloroacefic acid (CAA, 1) in DMSO is added to a ten-fold molar excess of ethylene diamine (EDA, 2) to afford the monoacid (3), which is isolated as a free base (or zwitterion). One equivalent of HCl is produced in this condensation. The second step is addition of cyanamide in water to the intermediate monoacid (3) to afford, after loss of ammonia, cyclocreatine (5). In the manufacturing process the product is purified by slurry in water.

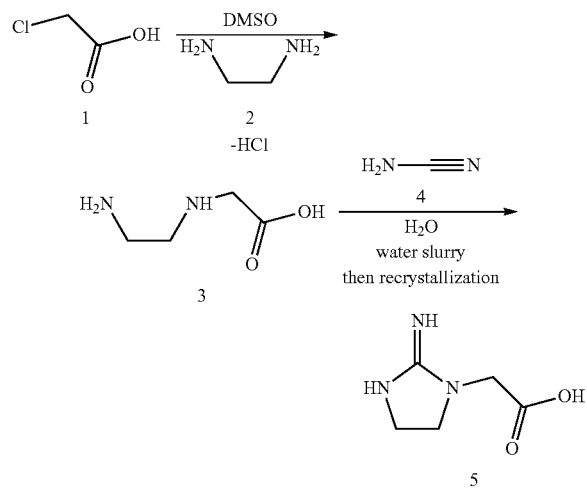

Step 1, Run 1

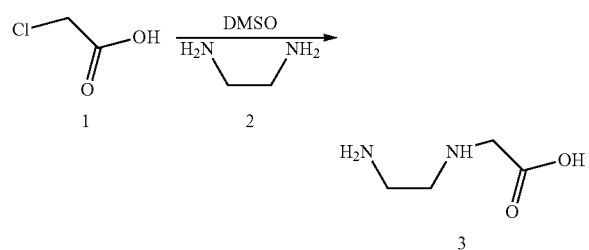

Preparation of [(2-Aminoethyl)amino]acetic Acid 3

A 1 L Erlenmeyer flask was charged with CAA (1) (500.7 g, 5.30 mol, 1.0 eq, Sigma-Aldrich) and DMSO (520.7 g). A solution was achieved by swirling the flask intermittently. A 5 L flask, fitted with nitrogen inlet, mechanical stirrer, thermocouple, and peristaltic metering pump was charged with EDA (2, 3182 g, 52.9 mol). Cooling of the 5 L flask (ice/water) was initiated. Addition of the solution of 1 in DMSO was started via the metering pump. See Table 1 for details.

TABLE 1

Addition data

| Entry | Time | Amount added, g | Temperature, °C | Addition Rate, g/hr |
|---|---|---|---|---|
| 1 | 1300 | 0 | 19.2 | NA |
| 2 | 1315 | 20 | 17.4 | 80 |
| 3 | 1327 | 58 | 17.3 | 190 |

TABLE 1-continued

Addition data

| Entry | Time | Amount added, g | Temperature, °C | Addition Rate, g/hr |
|---|---|---|---|---|
| 4 | 1400 | 150 | 21.6 | 182 |
| 5 | 1427 | 232 | 13.0 | 167 |
| 6 | 1501 | 324 | 10.4 | 162 |
| 7 | 1536 | 420 | 12.7 | 165 |
| 8 | 1556 | 474 | 15.1 | 162 |
| 9 | 1610 | 514 | 14.1 | 171 |
| 10 | 0824 (next day) | 970 | 21.3 | NA |

There was some solution remaining in the transfer line after the overnight charge. This solution was transferred to the 5 L flask. The reaction mixture was concentrated by rotary evaporation (53 to 60° C., 10 to 21 Torr) to remove EDA. Total amount of distillate collected was 2376 g. The residue (1800 g) was transferred back to the 5 L flask using DMSO (3010 g) as a wash. The internal temperature was 27° C. and the mixture had turned cloudy. Cooling of the 5 L flask (ice/water) was started. The mixture was stirred overnight. The resulting suspension was vacuum filtered through filter paper. Filtration took 36 minutes. The flask and solids were washed twice with DMSO (507.6 g, 501.7 g). Solids were washed twice with isopropanol (IPA, 448.4 g, 430.1 g). Solids were washed twice with tert-butylmethyl ether (TBME, 395.0 g, 406.3 g). The solids were dried under house vacuum with nitrogen bleed at ~35° C. for 3 days. Recovery of 3 (white solid) was 462.9 g (3.92 mol, 74%). $^1$H NMR (400 MHz, D$_2$O) δ 3.13 (s, 2H), 2.89 (apparent t, 2H, J=6 Hz), 2.76 (apparent t, 2H, J=6 Hz).

Step 1, Run 2

Preparation of [(2-Aminoethyl)amino]acetic Acid 3

A 1 L Erlenmeyer flask was charged with CAA (1) (499.1 g, 5.28 mol, 1.0 eq, Sigma-Aldrich) and DMSO (528.9 g). A solution was achieved by swirling the flask intermittently. A 5 L flask, fitted with nitrogen inlet, mechanical stirrer, thermocouple, and peristaltic metering pump was charged with EDA (2, 3186 g, 53.0 mol). Cooling of the 5 L flask (ice/water) was initiated. Addition of the solution of 1 in DMSO was started via the metering pump. See Table 2 for details.

TABLE 2

Addition data

| Entry | Time | Amount added, g | Temperature, °C | Addition Rate, g/hr |
|---|---|---|---|---|
| 1 | 1343 | 0 | 14.6 | NA |
| 2 | 1358 | 40 | 12.4 | 160 |
| 3 | 1417 | 92 | 10.0 | 164 |
| 4 | 1458 | 208 | 11.1 | 170 |
| 5 | 1540 | 326 | 9.7 | 169 |
| 6 | 1610 | 404 | 9.5 | 156 |
| 7 | 0839 (next day) | 988 | 22.2 | NA |

There was some solution remaining in the transfer line after the overnight charge. This solution was transferred to the 5 L flask. The reaction mixture was concentrated by rotary evaporation (53 to 60° C., 10 to 21 Torr) to remove EDA. The residue (2106 g) was transferred back to the 5 L flask using DMSO (3002 g) as a wash. The internal temperature was 26° C. and the mixture had turned cloudy. Cooling of the 5 L flask (ice/water) was started. The mixture was stirred overnight. The resulting suspension was vacuum filtered through filter paper. Filtration took 22 minutes. The flask and solids were washed twice with DMSO (498 g, 498 g). Solids were washed twice with IPA (384 g, 400 g). Solids were washed twice with TBME (360 g, 300 g). The solids were dried under house vacuum with nitrogen bleed at ~40° C. for 22 h. Recovery of 3 (white solid) was 454 g (3.84 mol, 73%). $^1$H NMR (400 MHz, D$_2$O) δ 3.13 (s, 2H), 2.89 (apparent t, 2H, J=6 Hz), 2.76 (apparent t, 2H, J=6 Hz).

Step 2

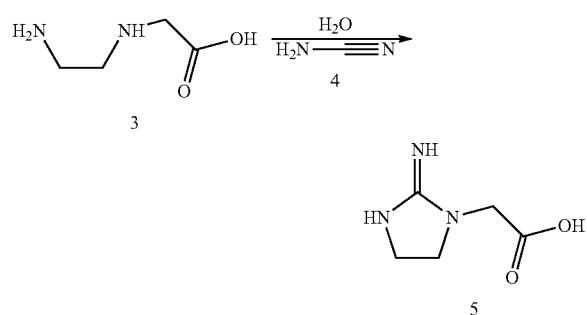

Preparation of (2-Iminoimidazolidin-1-yl)acetic Acid (5)

A 5 L flask, equipped with nitrogen sparge, reflux condenser, mechanical stirrer, thermocouple, and heating mantle, was charged with compound 3 (916 g, 7.75 mol, 1.00 eq) and D. I. water (918 g). The resulting slurry was heated with a target temperature of 60° C. Cyanamide (4, 50 wt % solution in water, 656 g, 7.80 mol, 1.01 eq) was charged according to Table 3.

TABLE 3

Addition data

| Entry | Time | Temp, ° C. | Volume of 4 added, mL |
|---|---|---|---|
| 1 | 1040 | 60.9 | 0 |
| 2 | 1043 | 59.7 | 85 |
| 3 | 1046 | 60.3 | 85 |
| 4 | 1056 | 61.4 | 185 |
| 5 | 1104 | 65.1 | 185 |
| 6 | 1107 | 66.3 | 220 |
| 7 | 1122 | 67.3 | 220 |
| 8 | 1132 | 67.3 | 350 |
| 9 | 1141 | 70.9 | 350 |
| 10 | 1157 | 71.6 | 575 |
| 11 | 1203 | 71.9 | 575 |
| 12 | 1214 | 74.1 | 750 |
| 13 | 1227 | 78.4 | 750 |
| 14 | 1323 | 62.5 | 750 |

The reaction was stirred at 60° C. for 3 h. Analysis by LCMS showed consumption of 3 and the absence of an intermediate with a mass of 160. The heat was shut off and the reaction was allowed to cool overnight with stirring. The mixture was vacuum filtered through filter paper. Filtration took 1.3 h. The flask and solids were washed with D. I. water (302 g). The wet solids were transferred to the cleaned 5 L flask. D. I. water (917.4 g) was added and the thick slurry was stirred at ambient temperature for 2 h. The mixture was vacuum filtered through filter paper (filtration took 45 min). The flask and solids were washed with IPA (696.1 g). The wet solids were transferred to the cleaned 5 L flask for a second slurry. D. I. water (916 g) was added and the thick slurry was stirred at ambient temperature for 2 h. The mixture was vacuum filtered through filter paper (filtration took 1.3 h). The flask and solids were washed with IPA (380 g). The product was air dried on the filter for 1 hour then dried in a vacuum oven (45° C., 25 in Hg, 2 days) to give 5 as a white solid (543.9 g, 3.80 mol, 49%). $^1$H NMR (400 MHz, D$_2$O) δ 3.53 (s, 2H), 3.62-3.55 (m, 2H), 3.53-3.46 (m, 2H).

Recrystallization of (2-Iminoimidazolidin-1-yl)acetic Acid (5)

A 5 L flask, equipped with reflux condenser, mechanical stirrer, thermocouple, and heating mantle, was charged with compound 5 that was twice re-slurried (141.8 g) and D. I. water (1414.5 g). The resulting slurry was heated with a target temperature of 100° C. When the temperature had reached 99.1° C., all of the solids had appeared to dissolve. The resulting hot solution was vacuum filtered through filter paper. Solids started to form in the filtrate after ~5 min. The resulting suspension was allowed to cool to ambient temperature over 23.5 h. The suspension was vacuum filtered through filter paper. The flask and solids were washed with D. I. water (104.7 g). The solids were dried in a vacuum oven (~40° C., ~27 in Hg) for 21.2 h, until constant weight was achieved. Recovery of 5 was 113.9 g (80.3%).

Example 9

Alternative Embodiment for Preparation of Cyclocreatine

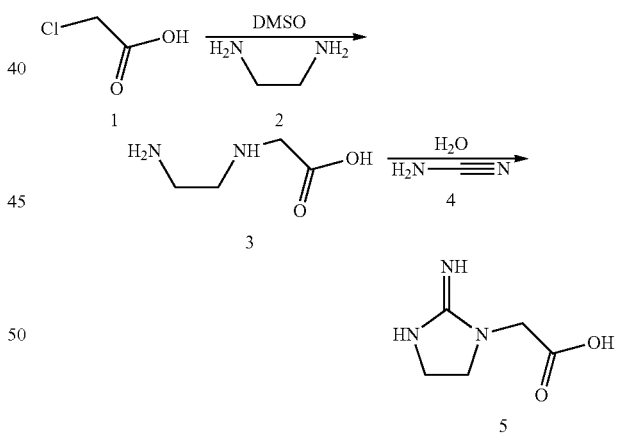

Preparation of [(2-Aminoethyl)amino]acetic Acid 3

A solution of chloroacetic acid (1) was prepared by dissolving 1 (500.0 g, 5.29 mol, 1.0 equiv) in DMSO (515.6 g). A 5 liter flask, fitted with nitrogen inlet, mechanical stirrer, thermocouple, and peristaltic metering pump was charged with ethylenediamine (2, EDA, 3537 mL, 52.9 mol). Cooling (ice/water) was initiated. Addition of the solution of 1 in DMSO was started via the metering pump. See Table 1 for addition times, temperatures, and volumes remaining.

TABLE 1

| Entry | Time | Temperature, ° C. | Volume of 1 remaining |
|---|---|---|---|
| 1 | 10:51 | 17 | |
| 2 | 11:28 | 18 | |
| 3 | 12:18 | 16 | 720 |
| 4 | 13:38 | 11 | 625 |
| 5 | 14:35 | 12 | 550 |
| 6 | 15:17 | 10 | 490 |
| 7 | 16:08 | 8 | 420 |
| 8 | 8:59 (next day) | 19 | 0 |

The reaction mixture was concentrated by rotary evaporation (50 to 60° C., 14 to 21 torr) to remove EDA. Total amount of distillate collected was 2400 mL. Toluene (900 mL) was added to the residue and the mixture was concentrated by rotary evaporation (60° C., 30 torr) to azeotrope any remaining EDA. The residue was transferred back to the 5 liter flask using DMSO (3 kg) as a wash. The internal temperature was 28° C. and the mixture had turned cloudy. Cooling (ice/water) was started. The mixture was stirred overnight. The resulting suspension was filtered through filter paper. Filtration took 25 minutes. The flask and solids were washed with DMSO (2×500 mL). Solids were washed with isopropanol (IPA, 2×500 mL). Solids were washed with tert-butylmethyl ether (TBME, 2×500 mL). The solids were dried under high vacuum at ambient temperature for 18 hours. Recovery of 3 (white solid) was 480.4 g (59%). NMR analysis showed 92.4 mol % 3, 6.4 mol % EDA, and 1.1 mol % N,N'-diacetic acid of EDA. $^1$H NMR (400 MHz, D$_2$O) δ 3.13 (s, 2H), 2.89 apparent t (2H, J=6 Hz), 2.76 (apparent t, 2H, J=6 Hz).

Preparation of (2-Iminoimidazolidin-1-yl)acetic acid (5)

A 5 liter flask, equipped with nitrogen inlet, reflux condenser, mechanical stirrer, ther uocouple, and heating mantle, was charged with compound 3 (478.4 g, 4.05 mol, 1.00 equiv) and D. I. water (484.5 g). The resulting slurry was stirred at ambient temperature (22° C.). Cyanamide (4, 50 wt % solution in water, 340.5 g, 4.05 mol, 1.00 equiv) was charged in one portion. The addition of the cold solution dropped the internal temperature to 15° C. The reaction mixture had become a solution. Heating was started. The target temperature was 40° C. After 22 minutes the internal temperature had risen to 62° C. Heating was stopped. Table 2 shows the progress of the exotherm and reaction.

TABLE 2

| Entry | Time | Temp, ° C. |
|---|---|---|
| 1 | 9:28 | 15 |
| 2 | 9:50 | 62 |
| 3 | 9:56 | 70 |
| 4 | 10:01 | 80 |
| 5 | 10:08 | 84 |
| 6 | 11:48 | 71 |
| 7 | 13:05 | 70 |

Analysis by LCMS showed consumption of 3 and the absence of an intermediate with a mass of 160. The heat was shut off and the reaction was cooled in an ice/water bath. The mixture was stirred overnight. The mixture was filtered through filter paper. Filtration took 25 minutes. The flask and solids were washed with D. I. water (150 mL). The wet solids were transferred to a 2 liter flask, equipped with a mechanical stirrer. D. I. water (450 mL) was added and the thick slurry was stirred at ambient temperature for 3 hours. The mixture was filtered through filter paper (filtration took 45 min). The flask and solids were washed with IPA (450 mL). The product was air dried on the filter for 1 hour then dried in a vacuum oven (40° C., 25 in Hg, 3 days) to give 5 as a white solid (248.9 g, 56%). $^1$H NMR (400 MHz, D$_2$O) δ 3.53 (s, 2H), 3.62-3.55 (m, 2H), 3.53-3.46 (m, 2H).

It is to be understood that the invention is not limited to the particular embodiments of the invention described above, as variations of the particular embodiments may be made and still fall within the scope of the appended claims.

We claim:

1. A process for the preparation of a compound of formula (I):

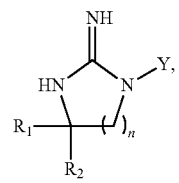

or a pharmaceutically acceptable salt thereof, comprising the step of reacting a compound of formula (II):

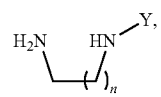

with a compound of formula (III):

wherein:

Y is CH$_2$CONR$_1$R$_2$ or CH$_2$CO$_2$R$_1$;

R$_1$, R$_2$, independently of each other, is hydrogen, lower alkyl, C$_7$-C$_{12}$ alkyl or cycloalkyl;

n is 1, 2, 3, 4 or 5; and wherein a carbon within the parentheses in the compound of formula (I) is optionally substituted with R$_3$ and R$_4$, each of which independently of each other is hydrogen, lower alkyl or cycloalkyl.

2. The process according to claim 1, wherein a carbon within the parentheses in the compound of formula (I) is substituted with R$_3$ and R$_4$, each of which independently of each other is hydrogen, lower alkyl or cycloalkyl.

3. The process according to claim 1, wherein n is 1.

4. The process according to claim 1, wherein the compound of formula (I) is cyclocreatine or a pharmaceutically acceptable salt thereof.

5. The process according to claim 1, wherein said compound is a compound of formula (Ia):

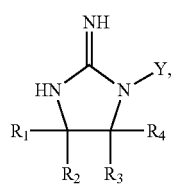 (Ia)

wherein:
Y is $CH_2CONR_1R_2$ or $CH_2CO_2R_1$;
$R_1$, $R_2$, $R_3$, $R_4$, independently of each other, is hydrogen, lower alkyl, $C_7$-$C_{12}$ alkyl or cycloalkyl,
or a pharmaceutically acceptable salt thereof.

6. The process according to claim 1, further comprising a precursor step of reacting ethylenediamine with chloroacetic acid to produce said compound of formula (II).

7. The process according to claim 6, wherein the concentration of cyanamide is 1-20 molar equivalents relative to a molar charge of said chloroacetic acid.

* * * * *